US009182411B2

(12) United States Patent
Colen

(10) Patent No.: US 9,182,411 B2
(45) Date of Patent: Nov. 10, 2015

(54) METHODS AND APPARATUS FOR THE DETECTION AND DIFFERENTIATION OF NON-SIALATED PROTEINS FROM SIALATED PROTEINS IN A FLUID SAMPLE

(75) Inventor: Chaim BenJoseph Colen, Grosse Pointe Woods, MI (US)

(73) Assignee: COLEN INNOVATIONS, L.L.C., Grosse Pointe Woods, MI (US)

( * ) Notice: Subject to any disclaimer, the term of this patent is extended or adjusted under 35 U.S.C. 154(b) by 533 days.

(21) Appl. No.: 12/824,827

(22) Filed: Jun. 28, 2010

(65) Prior Publication Data

US 2011/0015089 A1   Jan. 20, 2011

Related U.S. Application Data

(60) Provisional application No. 61/225,523, filed on Jul. 14, 2009.

(51) Int. Cl.
| C12M 1/34 | (2006.01) |
| G01N 27/00 | (2006.01) |
| B01L 3/00 | (2006.01) |
| G01N 33/68 | (2006.01) |

(52) U.S. Cl.
CPC ...... *G01N 33/6893* (2013.01); *B01L 3/502707* (2013.01); *B01L 2200/10* (2013.01); *B01L 2300/0681* (2013.01); *B01L 2300/087* (2013.01); *G01N 2333/79* (2013.01)

(58) Field of Classification Search
None
See application file for complete search history.

(56) References Cited

U.S. PATENT DOCUMENTS

| 5,585,275 A | 12/1996 | Hudson et al. |
| 5,629,213 A | 5/1997 | Kornguth et al. |

(Continued)

FOREIGN PATENT DOCUMENTS

WO    WO 03105899 A1    12/2003

OTHER PUBLICATIONS

Kilar, F. et al., "Fast and high resolution analysis of human serum transferrin by high performance isoelectric focusing in capillaries", Electrophoresis (1989), 10:23-29.*

(Continued)

*Primary Examiner* — Galina Yakovleva
*Assistant Examiner* — Gary E Hollinden
(74) *Attorney, Agent, or Firm* — Mintz, Levin, Cohn, Ferris, Glovsky and Popeo, P.C.

(57) ABSTRACT

The present invention is directed to methods and devices for detection of cerebrospinal fluid leaks by detection of the CSF protein beta-2 transferrin. The microfluidic devices and methods of the invention combine capture and specific labeling of transferrin from a sample with a subsequent step of isoelectric focusing to separate transferrin isoforms for detection. Microfluidic channels and chambers are patterned on a substrate, designed so that on one region (i.e., a microfluidic channel or chamber) of the substrate transferrin is selectively captured from the sample and labeled, and in a second region of the substrate, transferrin isoforms are separated using isoelectric focusing. Detection of two transferrin bands, indicating the presence of beta-2-transferrin, indicates the presence of CSF in the sample. The devices and methods of the invention provide a safe, efficient, and ultrarapid modality with high specificity and sensitivity for the detection of CSF in the acute care setting.

12 Claims, 5 Drawing Sheets

(56) References Cited

U.S. PATENT DOCUMENTS

| | | | |
|---|---|---|---|
| 5,776,748 | A | 7/1998 | Singhvi et al. |
| 5,900,160 | A | 5/1999 | Whitesides et al. |
| 5,975,856 | A | 11/1999 | Welle |
| 6,007,302 | A | 12/1999 | Welle |
| 6,060,121 | A | 5/2000 | Hidber et al. |
| 6,180,239 | B1 | 1/2001 | Whitesides et al. |
| 6,586,232 | B2 | 7/2003 | Tom-Moy et al. |
| 6,645,432 | B1 | 11/2003 | Anderson et al. |
| 6,969,850 | B2 | 11/2005 | Staats |
| 7,233,000 | B2 | 6/2007 | Nassiopoulou et al. |
| 7,267,938 | B2 | 9/2007 | Anderson et al. |
| 7,323,143 | B2 | 1/2008 | Anderson et al. |
| 8,068,991 | B2* | 11/2011 | Jung et al. .......... 702/19 |
| 8,486,247 | B2* | 7/2013 | Kayyem .......... 204/452 |
| 8,859,211 | B2* | 10/2014 | Chaffey et al. .......... 435/7.1 |
| 2003/0102215 | A1* | 6/2003 | Bukshpan et al. .......... 204/459 |
| 2004/0002168 | A1 | 1/2004 | Remington et al. |
| 2004/0031686 | A1* | 2/2004 | Foret et al. .......... 204/548 |
| 2004/0072278 | A1* | 4/2004 | Chou et al. .......... 435/29 |
| 2004/0203079 | A1 | 10/2004 | Pentyala |
| 2006/0029978 | A1* | 2/2006 | O'Neill et al. .......... 435/7.1 |
| 2006/0210994 | A1* | 9/2006 | Joyce .......... 435/6 |
| 2007/0003992 | A1 | 1/2007 | Pentyala |
| 2007/0048795 | A1* | 3/2007 | Fang et al. .......... 435/7.1 |
| 2007/0196864 | A1 | 8/2007 | Pentyala |
| 2008/0017512 | A1* | 1/2008 | Bordunov et al. .......... 204/451 |
| 2009/0170092 | A1* | 7/2009 | Landers et al. .......... 435/6 |
| 2009/0194419 | A1* | 8/2009 | Huang et al. .......... 204/451 |
| 2011/0071036 | A1* | 3/2011 | Penterman et al. .......... 506/7 |
| 2012/0138469 | A1* | 6/2012 | Yager et al. .......... 204/548 |

OTHER PUBLICATIONS

Ren, K. et al., "Whole column fluorescence imaging on a microchip by using a programmed organic light emitting diode array as a spatial-scanning light source and a single photomultiplier tube as a detector", Lab Chip, (Aug. 2007), 7:1574-1580.*

Busto, E. et al., "Novel HPLC-ICP-MS strategy for the determination of beta-2-transferrin, the biomarker of cerebrospinal fluid (CSF) leakage", Analyst (May 2010), 135:1538-1540.*

Pillai S., Zhou G. X., Arnaud P., Jiang H., Butler W. J. & Zhang H. (1996) "Antibodies to endometrial transferrin and alpha 2-Heremans Schmidt (HS) glycoprotein in patients with endometriosis"; Am J Reprod Immunol, 35, 483 [published erratum appears in Am J Reprod Immunol Mar. 1997;37(3):277], Only abstract provided.

Nord et al, "Binding proteins selected from combinatorial libraries of an alpha-helical bacterial receiptor domain" (1997) Nat Biotechnol., 8:772-7, Only abstract provided.

Windman et al., "Microfluidics for ultrasmall-volume biological analysis," Adv. Chromatogr. 42:241-67 (2003).

Taniguchi et al., "Sugar chains of cerebrospinal fluid transferrin as a new biological marker of Alzheimer's disease"; Dement. Geriatr. Cogn. Disord. 26: 117-122 (2008), Only abstract provided.

Gornik, O. et al., "Change in transferrin sialylation is a potential prognostic marker for severity of acute pancreatitis"; Clin Biochem. 41:504-510 (2008), Only abstract provided.

C. Flahaut et al., "The effects of ethanol on the glycosylation of human transferrin"; Glycobiology 13: 191-198 (2003).

Freeze, H.H., "Genetic defects in the human glycome"; Nature Rev. Genet. 7:537-551 (2006), Only abstract provided.

Mathur S. P., Holt V. L., Lee J. H., Jiang H. & Rust P. F. (1998) "Levels of antibodies to transferrin and alpha 2-HS glycoprotein in women with and without endometriosis". Am J Reprod Immunol, 40, 69, Only abstract provided.

Beebe et al., "Microfluidic tectonics: a comprehensive construction platform for microfluidic systems," Proc. Natl. Acad. Sci. USA 97:13488-13493 (2000), Only abstract provided.

Becker et al., "Polymer microfabrication methods for microfluidic analytical applications," Electrophoresis 21:12-26 (2000), Only abstract provided.

Kohlheyer, D. et al. "Microfluidic high-resolution free-flow isoelectric focusing". Anal. Chem., 2007, vol. 79. pp. 8190-8198. See abstract, p. 8191 and fig. 1, Only abstract provided.

Sommer, G. J. et al. "IEF in microfluidic devices". Electrophoresis, Mar. 3, 2009, vol. 30, pp. 742-757. See abstract and p. 751.

Gorogh, T. et al. "Separation of beta2-transferrin by denaturing gel electrophoresis to detect cerebrospinal fluid in ear and nasal fluids". Clin. Chem., 2005, vol. 51, No. 9, pp. 1704-1710. See abstract and figs 2, 3.

Zahn, J.D. et al, "Microfabricated Polysilicon Microneedles for Minimally Invasive Biodmedical Devices"; Biomedical Microdevices, vol. 2, No. 4, (2000).

Fredman, Pam; "Detection of oligoclonal IgG bands in cerebrospinal fluid by immunofixation after isoelectric focusing on polyacrylamide gels with the PhastSystem"; Electrophoresis 1992, 13, 158-161.

Bethyl Laboratories, Inc.; Catalog No. A80-128; Human Transferrin Antibody Serum, 2 pages.

Press Release, "New Company Created to Develop Rapid CSF Detection Kit", Neuropro Technologies, Inc.; May 8, 2007.

* cited by examiner

METHODS AND APPARATUS FOR THE DETECTION AND DIFFERENTIATION OF NON-SIALATED PROTEINS FROM SIALATED PROTEINS IN A FLUID SAMPLE

CROSS-REFERENCE TO RELATED APPLICATIONS

This application claims the benefit of U.S. Ser. No. 61/225,523, filed Jul. 24, 2009, which application is fully incorporated herein by reference.

FIELD OF THE INVENTION

The present invention relates to methods and a device to distinguish non-sialated proteins from sialated proteins. An example of this is demonstrated through the detection of the presence or absence of cerebrospinal fluid (CSF) in a sample, in particular to the analysis of the CSF protein beta-2 transferrin.

BACKGROUND

The ability to rapidly distinguish non-sialated proteins from sialated proteins in a sample is vital to the management of various pathologies; such as; early detection of cerebrospinal fluid (CSF) leakage, endometriosis, melanoma, breast cancer, oral cancer, Alzheimer's disease and similar sialated/non-sialated protein or tau-protein diseases. CSF leakage refers to the escape of the fluid that surrounds the brain and spinal cord, and is caused by rupture of the membrane which surrounds the brain and spinal cord and contains the CSF. Head trauma is responsible for 50-80% of all cases of CSF leakage. Each year in the United States, over one million people are treated and released from hospital emergency departments with traumatic head injuries. Approximately 2 to 3% of head injuries result in the occurrence of CSF leaks; thus this is a relatively common condition seen in hospital emergency rooms. CSF leakage may also result from certain head, spine or brain surgeries, spinal taps, or accidental punctures during neural blockade. The main complication of CSF leakage is cerebral infection (meningitis and brain abscess), which occurs in 25-50% of cases. The prompt initiation of treatment with antibiotics and/or surgical treatment of fistulas is necessary to avoid severe complications. Appropriate treatment therefore requires a rapid and reliable method for determination of CSF leakage.

Radiologic methods, such as CT and MRI scans, can diagnose fractures and detect fluid levels within sinuses, thus suggesting, but not confirming cerebrospinal fluid leakage. Other radiologic techniques include contrast and radionuclide cisternography. Contrast cisternography can locate the site of leakage but may not detect intermittent leaks. Radionuclide cisternography is expensive, has a high false positive rate, and is not accurate in determining the location of leakage. Exploratory surgery, involving the detection of preoperative intrathecally applied fluorescein, is highly sensitive, but this invasive method may also entail some risks to the patient. Measurement of protein and glucose concentrations, such as glucose dipstick tests, have been used in the past as indicators for the presence of CSF. These methods are safe and non-invasive, but have poor reliability.

Beta-2-transferrin is a non-glycosylated (asialated) isoform of transferrin found only in cerebrospinal fluid, ocular fluids, and perilymph. The technology is still unavailable to raise antibodies to target and differentiate between glycosylated and non-glycosylated epitopes. Beta-2-transferrin may be separated from the sialated beta-1-transferrin isoforms and detected by immunofixation electrophoresis using antibodies that bind all transferrin isoforms. With a sensitivity of 94%-100%, and a specificity of 98%-100%, this assay has become the gold standard in detection of CSF leakage. However, because immunofixation electrophoresis is necessary to detect beta-2 transferrin, the assay is expensive ($230-300/sample), and carries multiple added costs for specimen handling, archiving, shipping and storage. Each sample must be provided in high volume, requiring as much as 1-2 ml of sample per assay. Moreover, special technical skills and experienced technicians are required to assure test precision and reliability, mandating that beta-2 transferrin assays be performed by specialty laboratories. As a result, turn-around time for results to reach the caregiver may take up to 4 days, often resulting in additional hospitalization time for the patient suspected of having a cerebrospinal fluid leak, who must remain in the hospital for monitoring until the test results are determined.

Endometriosis is a medical condition that affects 2 to 5 percent of all women. Cells lining the uterus or endometrium grow in other areas of the body, causing pain, irregular bleeding, and even infertility.

Currently, the only accurate diagnosis of the disease requires a laparoscopy, a procedure involving a "belly-button cut" and insertion of a lighted instrument into the navel. However a less invasive method would be the accurate and rapid diagnosis using the methods and the device described herein. Antibodies to the transferrin protein and α2-Heremans Schmidt glycoprotein (a 2-HSG) has been described (Pillai S., Zhou G. X., Arnaud P., Jiang H., Butler W. J. & Zhang H. (1996) Antibodies to endometrial transferrin and alpha 2-Heremans Schmidt (HS) glycoprotein in patients with endometriosis [published erratum appears in Am J Reprod Immunol 1997 March; 37(3):277]. Am J Reprod Immunol, 35, 483 and Mathur S. P., Holt V. L., Lee J. H., Jiang H. & Rust P. F. (1998) Levels of antibodies to transferrin and alpha 2-HS glycoprotein in women with and without endometriosis. Am J Reprod Immunol, 40, 69) and proposed as diagnostic markers.

Sialic acid-rich glycoproteins (sialoglycoproteins) bind selectin in humans and other organisms. Metastatic cancer cells often express a high density of sialic acid-rich glycoproteins. One example of the use of our methods and device may be in the diagnosis of melanoma. Melanoma is a malignant cancer of the skin. It is the eighth most common cancer in the United States and causes 1 to 2 percent of all cancer deaths. The diagnosis of melanoma is made on the basis of an excisional biopsy. However, not all excisional biopsies result in the diagnosis of melanoma. Also, recurrent nevus may be interpreted erroneously as a melanoma. HMB-45 is an antibody widely used in diagnostic pathology owing to its great specificity in identifying melanomas. Sialylation of antigen is crucial to HMB-45 binding, and suggests that the absence of staining in normal adult melanocytes, dermal nevi, and other melanocytic lesions may be a result of differential sialylation. Similarly, the differential detection of non-sialated and sialated proteins may aid in the rapid diagnosis of breast cancer, oral cancer, Alzheimer's disease and similar sialated/non-sialated protein or tau-protein diseases.

The present invention satisfies a need in the art by providing devices and methods for sensitive, specific and rapid detection of non-sialated protein in a patient sample using microfluidics technology.

SUMMARY OF THE INVENTION

The invention provides methods and devices for detection of the presence or absence of non-sialated protein, such as cerebrospinal fluid (CSF) in a sample, in particular by detecting the presence or absence of the CSF protein beta-2 transferrin, using microfluidics.

In an embodiment, the invention provides a microfluidic device for detection of non-sialated protein, such as cerebrospinal fluid (CSF) in a sample, comprising: a loading inlet for applying a sample into the microfluidic device; a capture/labeling chamber fluidically connected to the loading inlet, wherein the capture region comprises an immobilized capture agent for capture of transferrin proteins from the sample; an isoelectric focusing (IEF) chamber fluidically connected to the capture region and containing an IEF gel; and a detector operatively connected to the IEF chamber that detects the presence of transferrin bands within the IEF gel, wherein the detection of non-sialated protein, such as beta-2-transferrin indicates the presence of CSF in the sample. In embodiments, detection of non-sialated protein, such as beta-2-tranferrin comprises the detection of two transferrin bands.

In some embodiments, the microfluidic device further comprises a filter positioned such that the sample flows through the filter prior to entering the capture/labeling chamber. In some embodiments, the filter is a membrane, a mesh or a sieve. In some embodiments, the microfluidic device comprises a filtration chamber containing a gel or column packing material which allows proteins to flow through but blocks the flow of cells or particulate matter.

In various embodiments, the immobilized capture agent comprises antibodies, aptamers, affibodies, avimers or peptides, or a natural binding partner of non-sialated protein, such as transferrin, such as a transferrin receptor, or a portion thereof which retains specific binding activity for transferrin. In some embodiments, the capture agent is an antibody that specifically binds non-sialated protein, such as transferrin.

In some embodiments, the microfluidics device further comprises a reservoir containing a labeling agent, fluidically connected to the capture/labeling chamber. In various embodiments, the labeling agent is a chromogen, a catalyst, a fluorescent compound, a chemiluminescent compound, a radioactive element, a colloidal or dye particle, an enzyme, an enzyme substrate, or an organic polymer latex particle, liposome or other vesicle containing such signal producing substances.

In further embodiments labeling agent is a fluorophore, including but not limited to small molecular dyes, protein chromophores and quantum dots. In alternative embodiments, the labeling agent is a labeled antibody. In further embodiments, the antibody is labeled with a fluorophore.

In some embodiments, the microfluidics device further comprises a reservoir containing a release reagent, fluidically connected to the capture/labeling chamber. In some embodiments, the release reagent comprises a non-denaturing detergent in an aqueous buffered solution, in an amount sufficient to release captured proteins from the immobilized capture agent. In further embodiments, the buffer is compatible with isoelectric focusing.

In various embodiments, the non-sialated protein, such as transferrin isoforms are detected by colorimetric detection, enzyme-catalyzed production of colored or fluorescent dyes, microparticle/nanoparticle based detection using electron microscopy, AFM, or dark-field microscopy, magnetic detection using magnetic micro/nanoparticles, and electrical detection methods. Suitable labels are used in conjunction with these embodiments.

In some embodiments, the labeling agent is a fluorophore and the detector is a light emitting diode (LED)/photodetector grid array. In further embodiments, the LED photodetector grid array is positioned on a single face of the IEF gel path. In other embodiments, the LED/photodetector grid array is positioned above and below the IEF gel path.

In various embodiments, the microfluidics device includes one or more valves positioned in one or more channels. In various embodiments, the valves are mechanical, electrical, piezo-electric, hydraulic, or rotary valves, or rubber or elastomeric valves.

The invention also provides methods of detecting the presence or absence of non-sialated protein, such as CSF in a sample using a microfluidic device of the invention, the method comprising: applying the sample to the loading inlet of the microfluidic device; capturing transferrin proteins on the immobilized capture agent; eluting the captured protein from the immobilized capture agent to the IEF chamber; separating non-sialated protein isoforms, such as transferrin isoforms in the IEF chamber; and detecting the transferrin isoforms, wherein the detection of two transferrin bands indicates the presence of CSF in the sample.

In some embodiments, the method further comprises a filtration step prior to the capture step. In some embodiments, the method further comprises labeling the captured non-sialated protein, such as tranferrin proteins with a labeling agent. In some embodiments, the method comprises washing the captured non-sialated protein, such as tranferrin proteins with a release reagent containing a non-denaturing detergent to elute the captured proteins from the immobilized capture agents. In various embodiments the non-denaturing detergents include but are not limited to octadecyl maltoside, beta-octyl glucoside, or foscholine. In further embodiments, the method comprises one or more additional steps of washing with buffer, to remove unbound or non-specifically bound proteins, or to remove unbound labeling agent.

The invention further provides methods of using the devices and methods of the invention in the diagnosis of cerebrospinal leakage, endometriosis, melanoma, breast cancer, oral cancer, Alzheimer's disease and similar sialated/non-sialated protein or tau-protein diseases. CSF leakage is associated with a range of clinical conditions, including, for example, cerebrospinal fluid leaks associated with head trauma, cerebrospinal fluid leaks associated with concussion, bodily trauma with cerebrospinal fluid involvement, skull fractures with cerebrospinal fluid leak, cerebrospinal fluid leak following endoscopic endonasal surgery, cerebrospinal fluid leak following neurosurgery, cerebrospinal fluid leak following epidural catheter placement, spontaneous intracranial hypotension following cerebrospinal fluid leak, anthrax-induced intracranial hypotension with cerebrospinal fluid leak, cerebrospinal fluid leak-associated rhinorrhea, cerebrospinal fluid leak-associated otorrhea, cerebrospinal fluid leak associated with hydrocephalus, cerebrospinal fluid leak-associated intracranial neoplasms, or cerebrospinal fluid leak-associated congenital neural malformations.

DETAILED DESCRIPTION OF THE INVENTION

Definitions

Figure 1:
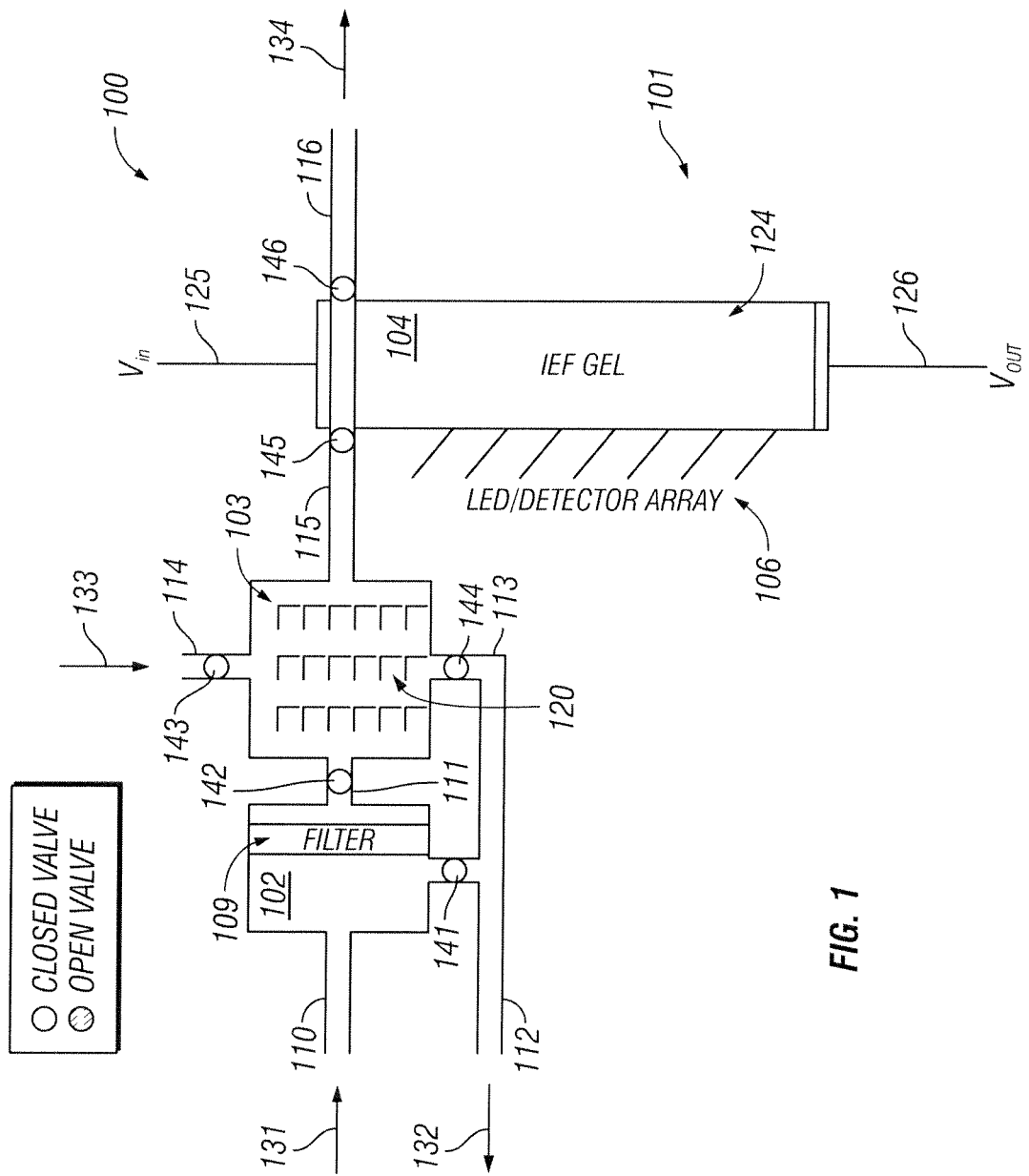
FIG. 1 is a schematic drawing showing an embodiment of a microfluidic device of the invention.
Figure 2:
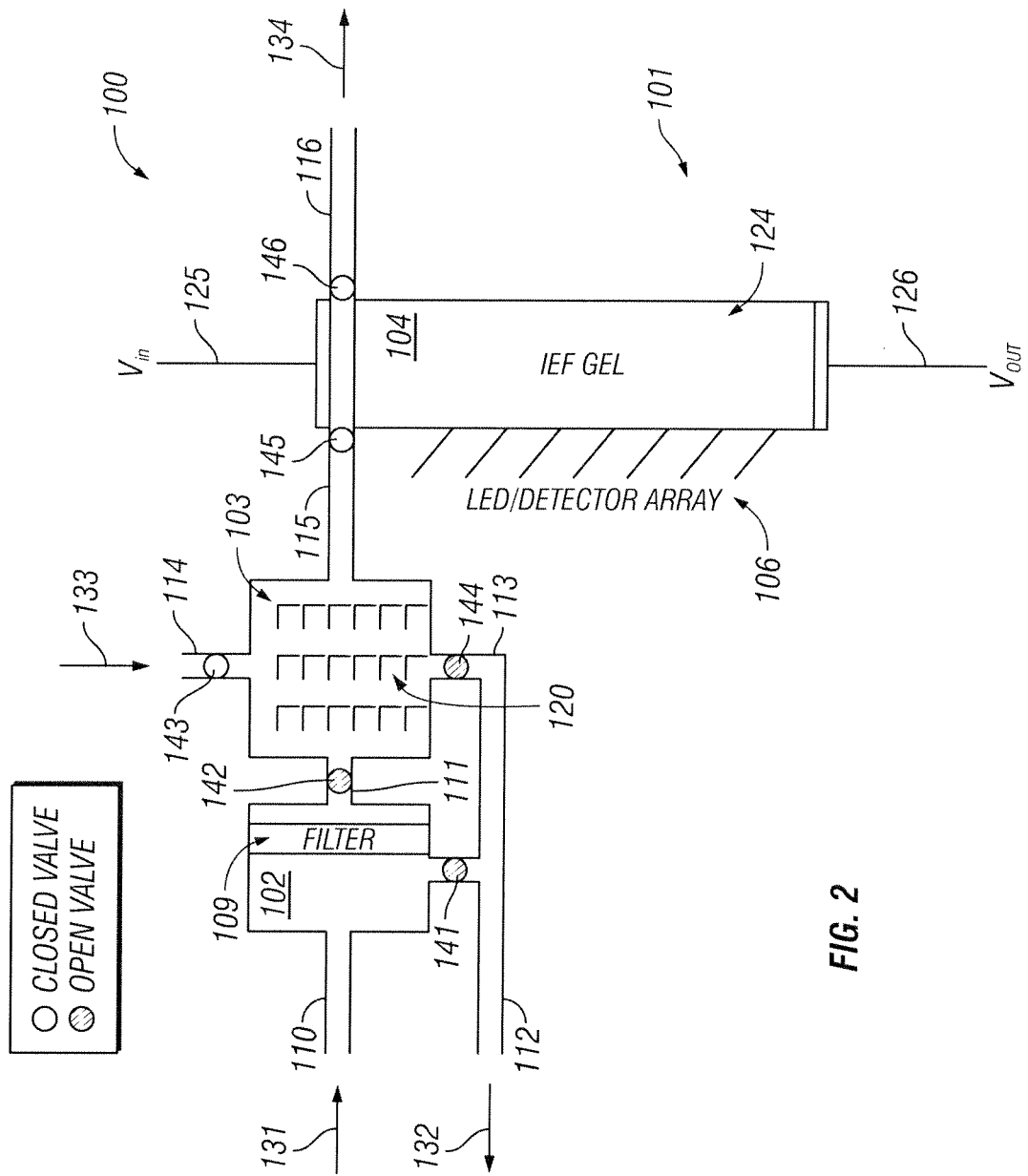
FIG. 2 is a schematic drawing showing a first stage in the operation of a microfluidic device according to an embodiment of the invention.

To facilitate an understanding of the present invention, a number of terms and phrases are defined below:

As used herein, the term "transferrin" refers collectively to all sialated and non-sialated protein isoforms, such as isoforms of the human transferrin protein (TF; GenBank Accession No. NP_001054).

As used herein, the term "beta-1 transferrin" refers to one or more sialated protein isoforms, such as isoforms of transferrin wherein the isoform has one or more sialic acid side residues.

As used herein, the terms "beta-2 transferrin" refers to one or more non-sialated protein isoforms, such as isoforms of human transferrin having no sialic acid side residues.

As used herein, the term "capture agent" refers to an agent that is immobilized onto a substrate and specifically binds to sialated and non-sialated protein, such as transferrin. Capture agents may include, for example, antibodies, affibodies, avimers, aptamers, and peptides, or a natural binding partner of sialated and non-sialated protein, such as transferrin, such as a transferrin receptor, or a portion thereof which retains specific binding activity for transferrin.

As used herein, the term "antibody" is used in its broadest sense to include polyclonal and monoclonal antibodies, as well as antigen binding fragments of such antibodies. An antibody useful in a method of the invention, or an antigen binding fragment thereof, is characterized, for example, by having specific binding activity for a sialated and non-sialated protein, such as transferrin epitope. Antibodies include naturally occurring antibodies as well as non-naturally occurring antibodies, including single chain antibodies, chimeric, bifunctional, and humanized antibodies, as well as antigen-binding fragments such as Fab, F(ab')$_2$, Fd and Fv fragments, that retain specific binding activity for a transferrin epitope.

A capture agent, such as an antibody, that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

As used herein, the term "label" refers to any substance which can be attached to specific binding agents, such as antibodies or antigens, which is capable of producing a signal that is detectable by visual or instrumental means. Various suitable labels for use in the present invention can include chromogens, catalysts, fluorescent compounds (such as, for example, fluorescein, phycobiliprotein, rhodamine), chemiluminescent compounds, radioactive elements, colloidal metallic (such as gold), non-metallic (such as selenium) and dye particles, enzymes, enzyme substrates, and organic polymer latex particles, liposomes or other vesicles containing such signal producing substances, and the like. Examples of enzymes that can be used as labels include phosphatases and peroxidases, such as alkaline phosphatase and horseradish peroxidase which are used in conjunction with enzyme substrates, such as nitro blue tetrazolium, 3,5',5,5'-tetranitrobenzidine, 4-methoxy-1-naphthol, 4-chloro-1-naphthol, 5-bromo-4-chloro-3-indolyl phosphate, chemiluminescent enzyme substrates such as the dioxetanes.

As used herein, the term "sample" refers to any sample suspected of containing non-sialated protein, such as cerebrospinal fluid, or a control sample, and may include, but is not limited to, any of the following: nasal fluid, aural fluid, blood, serum, cerebrospinal fluid, or fluid from a head or spinal wound or puncture.

As used herein, the term "fluidically connected" when used to describe a connection between regions, indicates that the regions are physically by a channel or path to allow fluid to flow from one region to the other.

As used herein, the term "channel" or "microchannel" refers to a structure providing a path effective to allow and/or guide flow of fluid therethrough.

As used herein, the term "buffer" refers to an aqueous solution containing either a weak acid and its salt, or a weak base and its salt, which is resistant to changes in pH.

As used herein, the term "detergent" refers to an amphipathic surface active molecule with polar and nonpolar hydrophobic domains, which binds strongly to hydrophobic molecules or molecular domains to confer water solubility. As used herein, the term "non-denaturing detergent" refers to a mild detergent such as a non-ionic detergent, characterized by an uncharged, hydrophilic headgroup, or a zwitterionic detergent, which contains both a positive an negative charge in their hydrophobic headgroup.

Microfluidics Devices

The microfluidic devices and methods of the invention combine capture and labeling of transferrin from a sample with a subsequent step of isoelectrofocusing to separate transferrin isoforms for detection. Microfluidic channels and chambers are typically patterned on a substrate, and may be designed so that on one region (i.e., a microfluidic channel or chamber) of the substrate transferrin is selectively captured from the sample and labeled, and in a second region of the susbstrate, transferrin isoforms are separated using isoelectrofocusing. Chambers and channels are fluidically connected to each other and to various reservoirs, inlets or outlets. Different embodiments will have different numbers of connections and hold, channel and direct fluid in alternative ways.

One embodiment of a microfluidic device of the invention is illustrated in FIG. 1. The microfluidic device 100 comprises substrate 101. Substrate 101 defines a filtering chamber 102, a capture/labeling chamber 103 and an isoelectrofocusing (IEF) chamber 104. The filtering chamber is fluidically connected at a first end by microchannel 110 to inlet 131 for the loading of a sample. In addition, filtering chamber 102 is fluidically connected at a second end to capture/labeling chamber 103, via microchannel 111, with valve 142 positioned therein. Filtration chamber 102 is also fluidically connected at a third end with microchannel 112. Microchannel 112, with valve 141 positioned therein, fluidically connects filtration chamber 102 with outlet 132.

The capture/labeling chamber 103 is fluidically connected at an end opposite to filtration chamber 102 with IEF chamber 104, through microchannel 115 with valve 145 positioned therein. Capture/labeling chamber 103 is additionally fluidically connected to inlet 133 through microchannel 114 with valve 143 therein, and to outlet 132 through microchannel 113 with valve 144 therein. IEF chamber 104 is fluidically connected at an end opposite to microchannel 115 to microchannel 116. Microchannel 116, with valve 146 fluidically connects IEF chamber 104 to outlet 134.

In various embodiments, inlet 131 is fluidically connected to one or more sample loading wells or ports. In various embodiments, inlet 133 is fluidically connected to one or more wells or reservoirs. These reservoirs may contain various reagents, including for example, buffers for washing away non-specific proteins that have not bound to the capture agents, buffers for washing away excess labeling agents, buffers suitable for IEF, labeling agents for labeling transferrin proteins, and reagents for releasing the captured transferrin from the immobilized capture agents. In various embodiments, outlet 132 and outlet 134 are fluidically connected to one or more waste wells.

Filtering chamber 102, capture/labeling chamber 103, and IEF chamber 104, although described for convenience as "chambers" may be either microfluidic channels or chambers. In some embodiments, the IEF chamber is a capillary having a diameter of about 5 μm to about 200 μm, and a length of about 5 mm to about 20 mm.

The capture/labeling chamber 103 includes immobilized capture agents 120 held therein. In an embodiment, capture/labeling chamber 103 includes a modified surface or affinity matrix for immobilization of capture agents 120. In an embodiment, capture/labeling chamber 103 includes one or more walls, floor, or ceiling (not shown) of capture/labeling chamber 103 which are modified to bind immobilized capture agents 120 upon contact therewith. In the embodiment illustrated in FIG. 1, capture/labeling chamber 103 has at least one modified surface with immobilized capture agents 120 bound thereto. In a further embodiment, capture/labeling chamber 103 includes an affinity matrix, such as but not limited to, membrane, beads or polymeric matrix wherein the immobilized capture agents bind upon contact therewith. In a still further embodiment, capture/labeling chamber 103 includes an affinity matrix bound with immobilized capture agents 120. Methods for immobilizing proteins, nucleic acids or other molecules on a surface of the device (e.g., within a microfluidic channel or chamber) are known in the art (see, for example, U.S. Pat. Nos. 5,629,213, 5,585,275 and 6,586,232). In some embodiments, the capture agent is irreversibly bound to the chamber surface. In some embodiments, the capture agent is coupled to a chemically modified solid using methods similar to those utilized for the preparation of ELISA assay plates. In alternative embodiments, the capture agent is reversibly bound, and is released with the transferrin to be resolved on the IEF gel.

Capture agent 120 is a known moiety which has selective binding affinity for transferrin. In some embodiments, the immobilized capture agent is an anti-transferrin antibody. Antibodies to human transferrin are commercially available. In other embodiments, the immobilized capture agent may be an affibody, an avimer, an aptamer, or a peptide. Affibodies are small protein domains selected by combinatorial approached for specific binding to a protein analyte. (Nord et al, (1997) Nat Biotechnol., 8:772-7.) Avimers™ are small, stable proteins that can act like antibodies and bind selectively to different receptors or ligands. Avimers are commercially available from Medimmune, Inc. and Avidia, Inc. Aptamers are oligonucleic acid or peptide molecules that bind a specific protein analyte. Aptamers are usually created by selecting them from a large random sequence pool using combinatorial screening techniques such as phage display or array technologies, but natural aptamers also exist. In other embodiments, the capture agent is a binding partner of transferrin, such as a transferrin receptor, or a portion thereof which retains specific transferrin binding activity.

IEF chamber 104 includes a separation medium 124 suitable to effect separation of proteins by isoelectric focusing. In isoelectric focusing, proteins are separated based upon their isoelectric point (pI). IEF gels effectively create a pH gradient so proteins separate according to their unique pI. A protein that is in a pH region below its (pI) will be positively charged and so will migrate towards the cathode. As the protein migrates, however, the charge will decrease until the protein reaches the pH region that corresponds to its pI. At this point the protein has no net charge and so its migration ceases. As a result, the proteins in a sample become focused into sharp stationary bands with each protein positioned at a point in the pH gradient corresponding to its pI. The technique is capable of extremely high resolution, with proteins differing by a single charge being fractionated into separate bands.

Suitable separation media for electrophoretic separations of proteins includes sieving matrices, such as polyacrylamide, agarose or sephadex. In such embodiments, separation medium 124 is generally prepared as a gel matrix also including an electrically-conductive buffer solution. A variety of these and other suitable separation media for electrophoresis of proteins are commercially available. In some embodiments, the gel contains polyacrylamide at a concentration of about 5% to about 10%. Buffers and reagents for IEF are commercially available from companies including AMRESCO, Invitrogen, GE Healthcare and Sigma-Aldrich. IEF chamber 104 additionally includes electrode connections 125 and 126. Electrodes suited for use in microfluidic devices are known in the art.

The IEF chamber 104 of the microfluidic device of the present invention may come in different lengths, widths, and depths, and contain different volumes of separation media. In various embodiments, the dimensions of the IEF chamber are selected to be sufficient to resolve transferrin isoforms in a typical sample. In various embodiments, the IEF chamber is between about 5 μm to about 25 μm in depth, between about 5 μm and about 300 μm in width, and about 5 mm and about 20 mm in length. In further embodiments, the IEF chamber is between about 10 mm and about 15 mm in length. In some embodiments, the IEF chamber is a capillary having a diameter of about 5 μm to about 200 μm, and a length of about 5 mm to about 20 mm.

In some embodiments, the device includes a filter 109 through which the sample flows prior to entering the capture/labeling chamber. In some embodiments, the filter is a membrane. When the filter 109 is a membrane, the filter 109 can be made of nylon, cellulose, cellulose ester, polyvinylidene difluoride (PVDF), polyethersulfone (PES), polytetrafluoroethylene (PTFE), polyester, polypropylene, polyethylene, or the like. The filter 106 can also be coated with hydrophobic or hydrophilic material. In some embodiments, the device of the invention comprises a filtration chamber fluidically connected to the capture/labeling chamber. In some embodiments, the filter is a membrane positioned at one end of the chamber.

In some embodiments, the filter 109 comprises a mesh or sieve. In some embodiments, the filtration chamber 109 comprises a gel or column packing material which allows proteins to flow through but blocks the flow of cells or particulate matter. In some embodiments, the filter is a microfiber filter. In some embodiments, the filter comprises a scaffold of microcolumns in the fluid path, spaced so as to block passage of red blood cells or white blood cells while allowing the passage of serum.

The microfluidic device further comprises detector 106. The detector is suitable for the detection of labeled transferrin proteins within the IEF gel, with the type of detector selected based upon the type of label used to label the transferrin proteins within the microfluidic device.

In some embodiments, the detection is carried via fluorescent-based readouts, in which the transferrin proteins are labeled with a fluorophore, including but not limited to small molecular dyes, protein chromophores and quantum dots. In some embodiments, the transferrin proteins are labeled with an antibody specific for transferrin that is labeled with a fluorophore.

A number of fluorescent dyes are commercially available, for example, the Alexa Fluor® dyes (Invitrogen, Carlsbad, Calif.). Other fluorescent labels that may be used in the invention include, but are not limited to, fluorescent lanthanide complexes, including those of Europium and Terbium, fluorescein, fluorescamine, rhodamine, tetramethylrhodamine, eosin, erythrosin, coumarin, methyl-coumarins, pyrene, Malacite green, stilbene, Lucifer Yellow, Cascade Blue™, Texas Red, 1,1'-[1,3-propanediylbis[(dimethylimino-3,1-propanediyl]]bis[4-[(3-methyl-2(3H)-benzoxazolylidene)methyl]]-,tetra-ioide, which is sold under the name YOYO-1, Cy and Alexa dyes, and others described in the 9th Edition of the Molecular Probes Handbook by Richard P. Haugland, hereby expressly incorporated by reference.

In embodiments wherein a fluorescent label is used, a light source is needed to excite the fluorescent label to emit radiation. A light source may be provided with the device, or the device may be used with an external light source for providing illumination for fluorescence measurements. As is known in the art, photodiodes, confocal microscopes, CCD cameras, or photomultiplier tubes may be used to image the radiation emitted by fluorescent labels.

In further embodiments, the label is a fluorescent label, and the detector is a light emitting diode (LED)/photodetector grid array. The LEDs generate radiation at a wavelength chosen to excite the fluorophore used as a label. In some embodiments, the LED/photodetector array is positioned both above and below the IEF gel. In alternative embodiments, the LED/photodetector array is positioned on a single face of the IEF gel. In some embodiments the output from the photodetector array is visualized on an LED screen in the form of either analog or digital signals. In other embodiments the output from the photodetector array is visualized on a liquid crystal display (LCD) screen. The LEDs used in the detector may be nearly any type of device such as, but not limited to, organic light emitting diodes, semiconductor light emitting diodes, laser diodes, solid state laser diodes, and combinations thereof.

In other embodiments, detection can be performed with methods other than fluorescence based techniques. Exemplary suitable techniques include colorimetric detection, enzyme-catalyzed production of colored or fluorescent dyes, microparticle/nanoparticle based detection using electron microscopy, AFM, or dark-field microscopy, magnetic detection using magnetic micro/nanoparticles, and electrical detection methods. Suitable labels are used in conjunction with these embodiments.

A number of methods and approaches are known for making microfluidic devices, including microassembly, bulk micromachining methods, surface micro-machining methods, standard lithographic methods, wet etching, reactive ion etching, plasma etching, stereolithography and laser chemical three-dimensional writing methods, soft lithography methods, modular assembly methods, replica molding methods, injection molding methods, hot molding methods, laser ablation methods, combinations of methods, and other methods known in the art. It will be apparent to those of skill in the art that a number of these approaches can be adapted for use according to the present invention. (See, for example, Madou M. J. "Fundamentals of microfabrication" CRC Press, Boca Raton (1997); Zahn, J. D. et al, Biomedical Microdevices, Vol. 2, No. 4, (2000); Chovan, et al., "Microfabricated devices in biotechnology and biochemical processing," Trends Biotechnol. 20:116-22 (2002); Windman et al., "Microfluidics for ultrasmall-volume biological analysis," Adv. Chromatogr. 42:241-67 (2003); Beebe et al., "Microfluidic tectonics: a comprehensive construction platform for microfluidic systems," Proc. Natl. Acad. Sci. USA 97:13488-13493 (2000); Becker et al., "Polymer microfabrication methods for microfluidic analytical applications," Electrophoresis 21:12-26 (2000); and U.S. Pat. Nos. 5,776,748, 5,900,160; 6,060,121; 6,180,239; 6,645,432; 6,969,850; 7,233,000; 7,267,938; and 7,323,143).

The microfluidic device of the invention comprises a number of channels and chambers. The channels and chambers can be manufactured to have various shapes and dimensions using, for example, well developed elastomer molding, photolithography or micro-machining methods. The geometry of a channel may vary widely and includes tubular passages with circular, rectangular, square, D-shaped, trapezoidal or other polygonal cross-sections. Channels are typically on the order of 1 um to 200 um in diameter, typically 10 um to 75 um in diameter, and approximately 0.1 to 50 cm in length. Chambers may have a volume of about 1 nl to about 100 ul, typically about 10 nl to 20 ul. The microfluidic device typically comprises a total area of from about 0.1 $cm^2$ to about 20 $cm^2$. In some embodiments the microfluidic device comprises a total area of from about 1 $cm^2$ to about 10 $cm^2$.

The microfluidic device may be made from substrates including glass, quartz, silicon, plastic or other polymeric material. In some embodiments, at least a portion of the microfluidic device comprises chemically surface modified plastic (for example, polypropylene or polystyrene) such as is typically used in the manufacture of ELISA plates for binding antibodies.

In certain embodiments, detector 106 is adapted for detection of fluorescent labels. In such embodiments, at least one surface of IEF chamber 104 in substrate 101 is formed of transparent materials. In embodiments wherein substrate 101 or portions thereof are formed of transparent materials, the transparent materials typically emit low fluorescence upon illumination with the light. Plastic microchannels or chambers made out of polydimethylsiloxane (PDMS) substrate are advantageous for isoelectric focusing because they are optically transparent at the wavelengths required for the fluorescence detection of proteins and they provide low fluorescence background. Other materials having suitable optical transparency may also be used.

In various embodiments, as shown in FIGS. 1-5, microfluidic device 100 includes one or more valves. In various embodiments, the valves are mechanical, electrical, hydraulic, or rotary valves, or rubber or elastomeric valves. In some embodiments, the valves include a thermoelectric device capable of providing either addition of heat or removal of heat, and a material capable of phase change upon addition of heat or removal of heat by the thermoelectric device. See, for example, U.S. Pat. Nos. 5,975,856 and 6,007,302.

Methods of Use of Microfluidic Devices of the Invention

The invention further provides methods for using devices and systems disclosed herein. The operation of an embodiment of FIG. 1 is described as follows. In an embodiment, microfluidic device 100 is primed with buffer or other fluid, and has been preloaded with capture agents 120 and IEF medium 124. In further embodiments, capture agents 120 are loaded into microfluidic device 100 via inlet 133. In further embodiments, the device includes additional inlet channels for loading capture agents 120 into capture/labeling chamber 103, or for loading IEF medium 124 into IEF chamber 104.

A sample, in a buffered solution, suspected to contain CSF, is loaded via inlet 131. In some embodiments, the sample volume is typically from about 100 µl to about 1 ml. The sample may be diluted in saline solution, with a pH of about 7.4. In some embodiments, with larger sample volumes (about 1 ml), the sample may be aspirated through the capture/labeling chamber of the device so that all transferrin is captured, and the residual fluid aspirated out of the device.

In some embodiments, the sample is centrifuged prior to application to the microfluidic device to remove cells. For example, a blood sample is centrifuged to remove red blood cells and white blood cells, and the plasma is applied to the device. In alternative embodiments, a blood sample is allowed to coagulate, and the plasma is then applied to the device.

Valves 141 and 142 are opened, and valves 143, 144, 145 and 146 are closed. The sample fills filtration chamber 102. Cells or particulate matter in the sample are filtered through filter 106 and the filtered sample enters capture/labeling chamber 103. In some embodiments, valve 142 is also open to allow displacement of fluid from filtering region 102. The filtered sample moves through 111 through valve 142 and into capture/labeling chamber 103, where transferrin protein in the sample binds to immobilized capture agents 120. In some embodiments, valve 144 is closed when the sample occupies capture/labeling chamber 103, for example when a volume of fluid approximately equal to that of capture/labeling chamber 103 is displaced by sample moving into capture/labeling chamber 103. In further embodiments, valve 144 is closed to contain the sample in capture/labeling chamber 103 for a period of time. In some embodiments, the period of time is equal to or in excess of time for binding equilibrium to be reached for binding of transferrin to capture agent 120. Valve 144 is then opened to allow unbound sample to exit through outlet channel 113.

Figure 3:
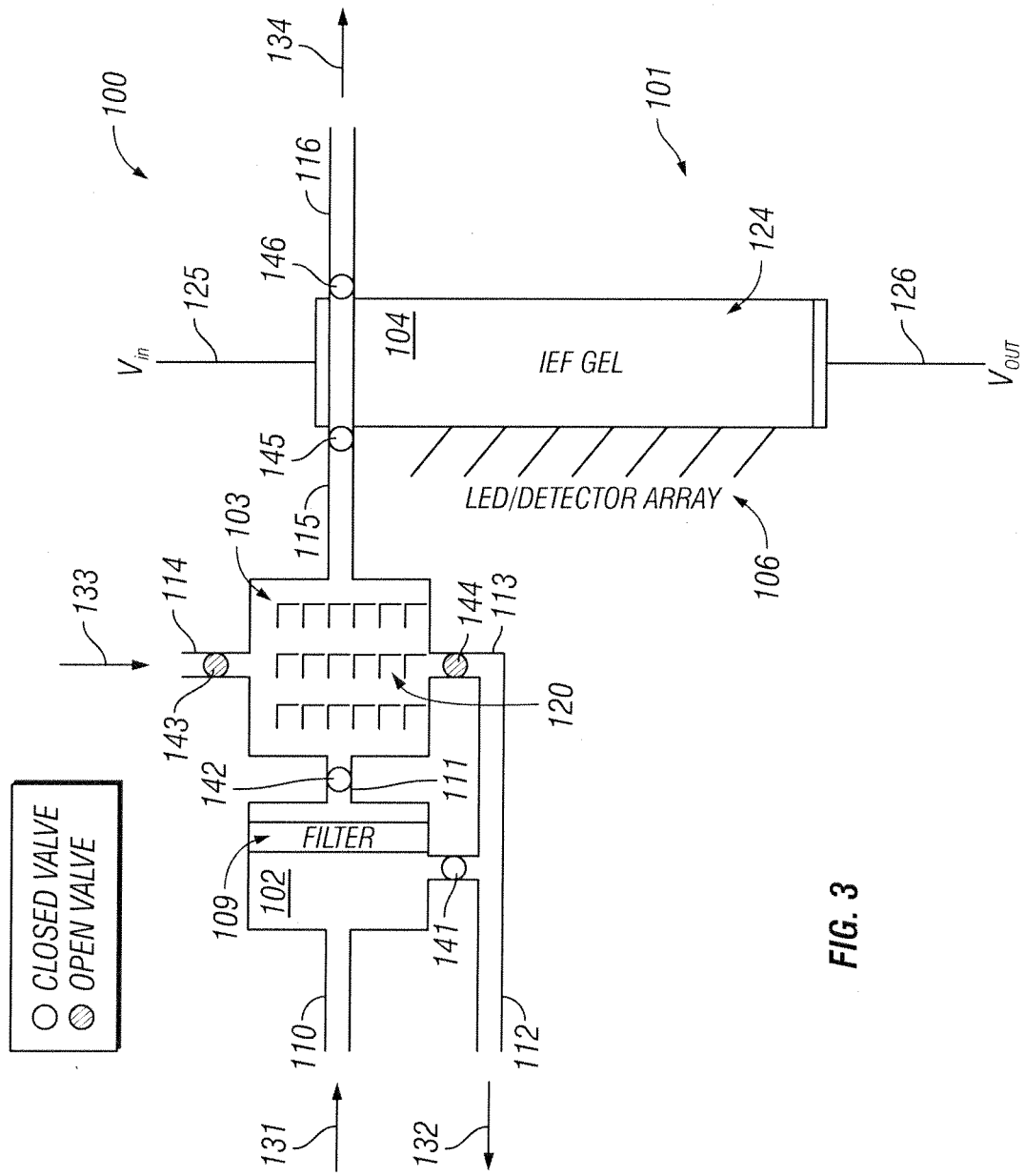
FIG. 3 is a schematic drawing showing a second stage in the operation of a microfluidic device according to an embodiment of the invention.

As shown in FIG. 3, valve 142 is closed to isolate capture/labeling chamber 103. Unbound and/or non-specifically bound sample, if present, moves out of capture/labeling region 103, typically by fluid pressure from buffered solution provided through inlet 133, and exits via outlet channel 113 through opened valve 144. Following this wash step, a labeling agent is admitted via inlet channel 114 through valve 143. In alternative embodiments, the labeling agent is provided from a reagent supply well fluidically connected to capture/labeling chamber 103 via another inlet channel (not shown). In some embodiments, valve 144 is closed for a period of time to contain the labeling agent in the chamber. In an embodiment, a period of time is equal to or in excess of time needed for binding equilibrium to be reached for binding of the labeling agent to transferrin. Chamber 103 is then washed by buffered solution provided through inlet channel 114 to remove spent/unreacted labeling agent.

In various embodiments, the labeling agent is a chromogen, a catalyst, a fluorescent compound (such as, for example, fluorescein, phycobiliprotein, rhodamine), a chemiluminescent compound, a radioactive element, a colloidal metallic (such as gold), non-metallic (such as selenium) or dye particle, an enzyme, an enzyme substrate, and organic polymer latex particles, liposomes or other vesicles containing such signal producing substances, and the like. In some embodiments, the labeling agent is an antibody that specifically binds transferrin, which antibody is attached to a label.

Figure 4:
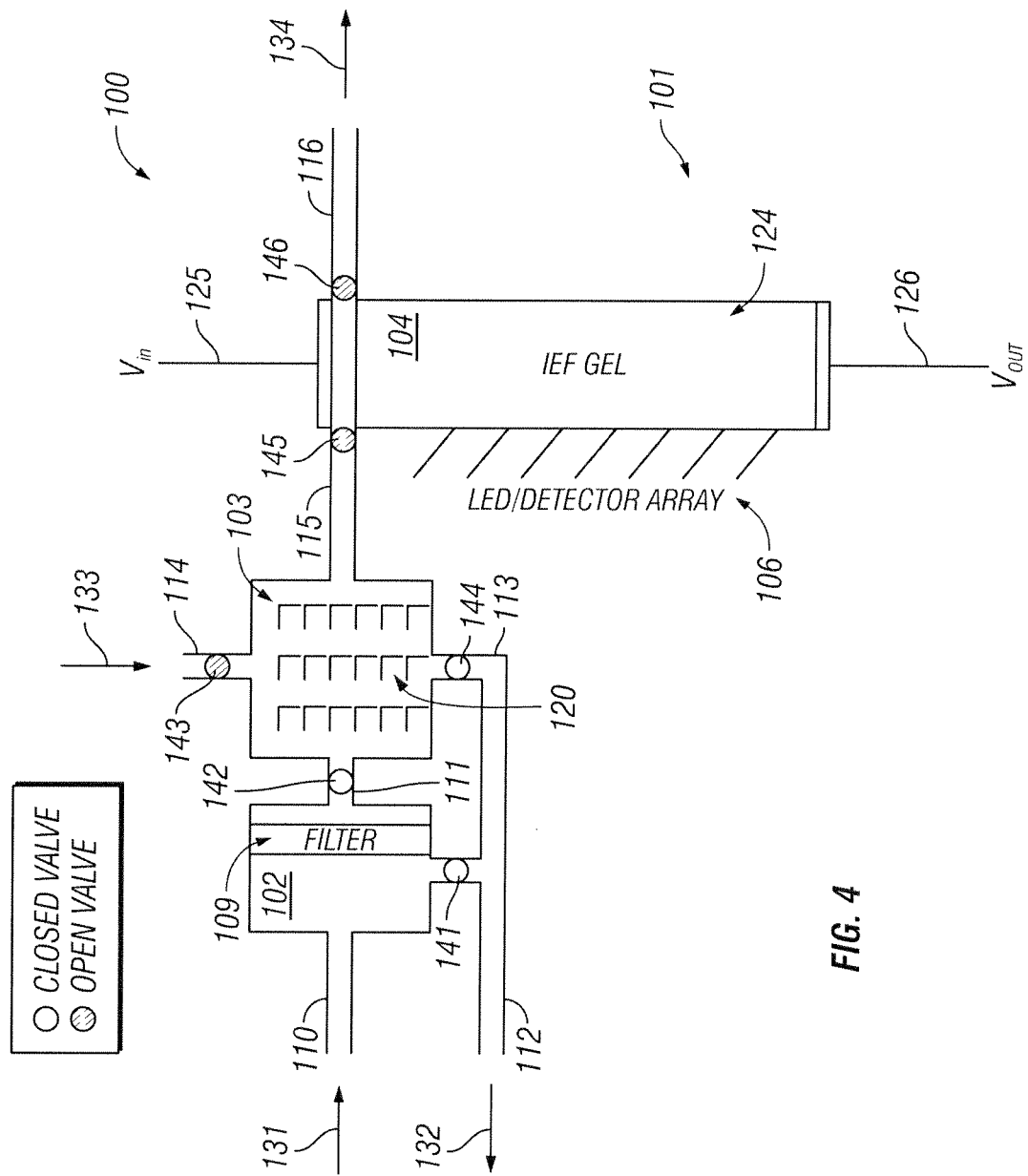
FIG. 4 is a schematic drawing showing a third stage in the operation of a microfluidic device according to an embodiment of the invention.

As shown in FIG. 4, valve 144 is closed, and valves 145 and 146 are opened to allow sample loading onto the IEF gel. A buffer comprising a non-denaturing detergent is provided through inlet channel 114, to release bound transferrin from the immobilized capture agents. In various embodiments, the release reagents comprise a non-denaturing detergent in a buffer. In various embodiments the non-denaturing detergents include but are not limited to glucosides, maltosides, polyoxyethylene glycols, glucamides, phosphine oxides, foscholines, dimethyl amines, dimethyl glycines, amine oxides, or TWEEN or TRITON detergents. Commercially available detergents include, for example, ANATRACE non-ionic and Zwitterionic detergents from Affymetrix (Santa Clara, Calif.).

In alternative embodiments, the release buffer is provided from a reagent supply well fluidically connected to capture/labeling chamber 103 via another inlet channel (not shown). The released labeled transferrin then moves to the IEF gel. In some embodiments, valve 144 is closed when the release buffer occupies capture/labeling chamber 103, to contain release buffer in capture/labeling region 103 for a period of time. In an embodiment, a period of time is equal to or in excess of time needed for dissociation equilibrium to be reached for dissociation of transferrin from capture agent 120. Valve 144 is then opened to allow loading of released labeled transferrin onto the IEF gel.

In some embodiments, the capture/labeling chamber 103 is then washed with a buffer suitable for IEF, provided through inlet channel 114. In alternative embodiments, the IEF buffer is provided from a reagent supply well fluidically connected to capture/labeling chamber 103 via another inlet channel (not shown). In other embodiments, the release buffer comprises the non-denaturing detergent within a buffer compatible with IEF (for example, a low salt buffer), so that only a single release/wash step is required.

Figure 5:
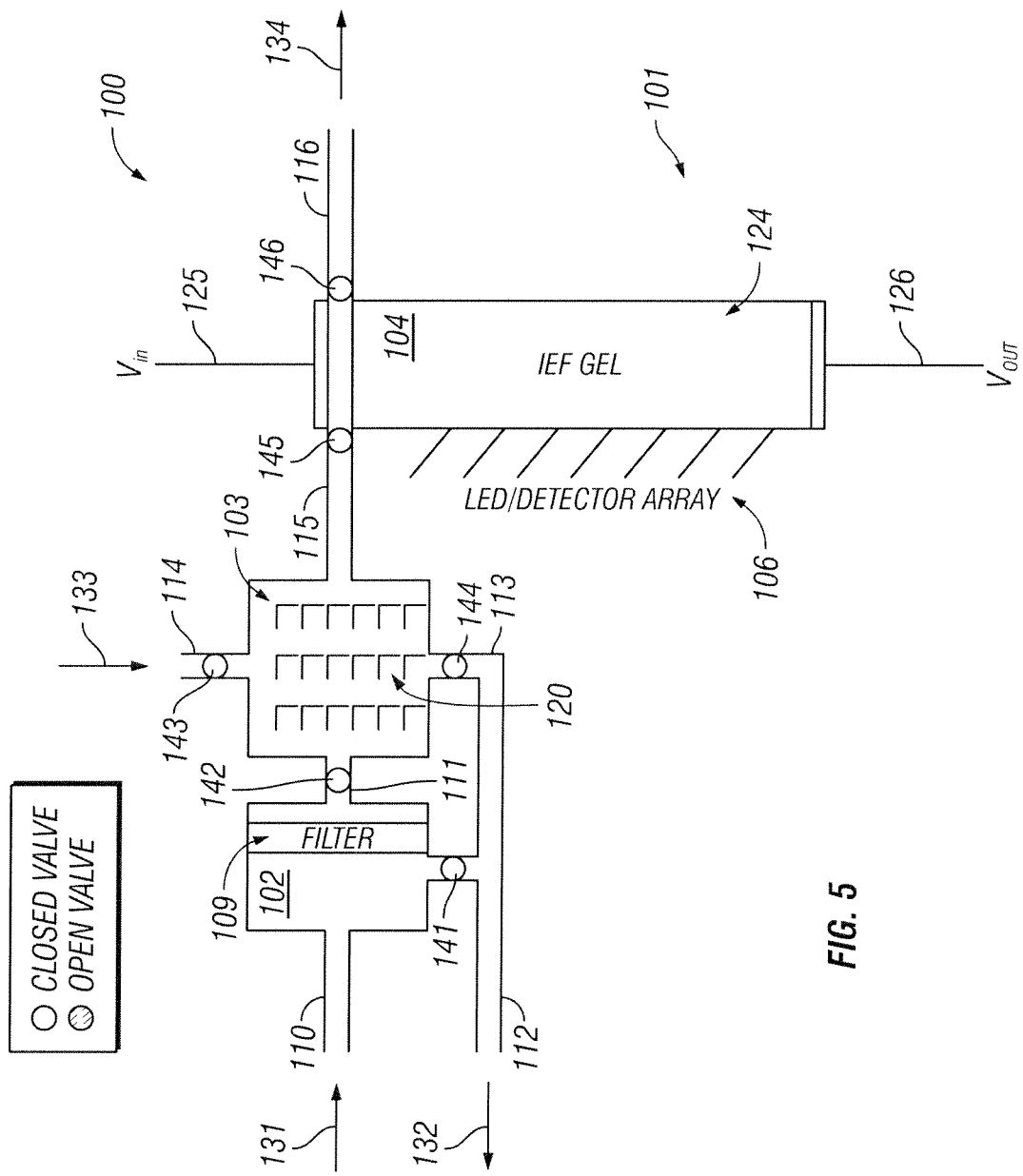
FIG. 5 is a schematic drawing showing a fourth stage in the operation of a microfluidic device according to an embodiment of the invention.

As shown in FIG. 5, valves 145 and 146 are closed to isolate IEF chamber 104. Voltage is applied to the IEF gel across electrodes 125 and 126. The voltage used in IEF is typically from 100 to 1000 V/cm. The specific voltage used is determined based upon the pH gradient and the length of the IEF gel. The voltage is applied for a time sufficient to provide separation o transferrin bands in a sample. Electrical power for the IEF may be supplied by any commercially available power supply and regulator or controller.

Following IEF of the sample, labeled transferrin bands are detected at detector 106. As disclosed in the art, beta-2-transferrin is a desialated isoform of transferrin found only in cerebrospinal fluid, ocular fluids, and perilymph. IEF serves to separate beta-2-transferrin from the sialated beta-1-transferrin isoforms. Detection of two transferrin bands is therefore indicative of the presence of CSF in the sample. In some embodiments, one or more control samples are also applied to the microfluidic device. In various embodiments, controls may include one or more of a sample containing beta-1 transferrin, a sample containing beta-2 transferrin, and a sample containing a combination of both beta-1 and beta-2 transferrin.

Additional embodiments of microfluidic device 100 differ in the number of additional interconnected components and defined points of entry and exit from the embodiments presented in FIGS. 1-5. Further additional embodiments may include, for example, additional microfluidic channels fluidically connected to additional reagent supply wells and terminal or waste wells. Other embodiments may include additional interconnected components to facilitate, control and direct fluidic connection. Further embodiments of FIGS. 1-5 include other valve configurations including more or fewer valves and/or alternative placement relative to regions and wells to operably separate regions, channels, and wells and/or to control direction and timing of movement of reagents, sample and portions thereof, into and through components of microfluidic device 100. Additional embodiments of FIGS. 1-5 may differ in operation, for example in sequence and timing of opening and closing of one or more of valves 141, 142, 143, 144, 145 and 146.

In most embodiments, movement of sample and reagents within the microfluidic device is mediated by fluid movement and/or pressure. In some embodiments, the movement of samples and reagents within the microfluidic device may be enabled by pumps, or by gas pressure to induce fluid flow, using methods known in the art.

The microfluidic device of the invention is typically operated at room temperature. In some embodiments, a heat sink above or below the device is used to stabilize the temperature of the device. In some embodiments, a Peltier type cooling system is incorporated into an external housing.

In various embodiments, the microfluidic device of the present invention is further connected to additional components, including, for example, a heat source, a detector source, a light source, pumps to provide pressure, power sources, and electrodes or electrode contacts for electrophoresis. Power supplies for electrophoretic applications are commercially available from companies including, for example, BioRad, GE Healthcare, Stratagene, and Thermo Fisher Scientific.

The devices and methods of the invention provide a safe, efficient, and ultrarapid modality with high specificity and sensitivity for the detection of CSF in the acute care setting. For example, the devices and methods of the invention may be used immediately after a trauma or a head injury to test for CSF leakage in a patient. They may also be used during-surgery or post-surgery, especially in head and brain surgery, or to test samples obtained during and after neural blockade.

In practice, the devices and methods of the invention are utilized in a variety of clinical settings to determine the presence of CSF in a sample, including skull fractures, CSF leaks following various surgeries, such as endoscopic endonasal surgery, neurosurgery, epidural catheter placement, spontaneous intracranial hypotension, anthrax induced intracranial hypotension, or CSF leaks associated conditions such as rhinnorhea and otorrhea, hydrocephalus, intracranial neoplasms, congenital neural malformations, and the like.

The devices and methods of the invention may also be utilized for the diagnosis of other diseases and conditions characterized by altered glycosylation levels of transferrin in a bodily tissue or fluid. For example, altered tranferrin glycosylation levels in CSF are found in patients with Alzheimer's disease. (Taniguchi et al., Dement. Geriatr. Cogn. Disord. 26: 117-122 (2008)). Change in transferrin sialation is also a potential prognostic marker for severity of acute pancreatitis (Gornik, O. et al., Clin, Biochem. 41:504-510 (2008). The appearance of hyposialated tranferrin fraction in plasma is a marker of chronic alcohol consumption (C. Flahaut et al., Glycobiology 13: 191-198 (2003), and a blood test for the glycosylation status of transferrin is also utilized as a marker in screening for congenital disorders of glycosylation. (Freeze, H. H., Nature Rev. Genet. 7:537-551 (2006).

The present invention is not to be limited in scope by the embodiments disclosed herein, which are intended as single illustrations of individual aspects of the invention, and any that are functionally equivalent are within the scope of the invention. Various modifications to the devices and methods of the invention, in addition to those described herein, will become apparent to those skilled in the art from the foregoing description and teachings, and are similarly intended to fall within the scope of the invention.

All patents, patent applications and publications cited in this application are hereby incorporated by reference herein their entirety for all purposes to the same extent as if each individual patent, patent application or publication were so individually denoted.

The invention claimed is:

1. A microfluidic device for detection of cerebrospinal fluid (CSF) in a sample, comprising:
    a microchannel with a loading inlet for loading the sample into the microfluidic device;
    a filtration chamber fluidically connected to the loading inlet, the filtration channel allowing proteins to flow through but block a flow of cells or particulate matter;
    a capture/labeling chamber fluidically connected to the filtration chamber and to a valve, the capture/labeling chamber including an immobilized capture agent for capture of transferrin proteins from the sample and which retains specific binding activity for transferrin, the capture/labeling chamber having at least one modified surface with the immobilized capture agents bound thereto, the capture/labeling chamber having an affinity matrix where the immobilized capture agents bind upon contact therewith;
    while in the capture/labeling chamber, transferrin protein in the sample binds to the immobilized capture agents with the valve remaining closed when the sample occupies the capture/labeling chamber for a period of time equal to or in excess of a time for a binding equilibrium to be reached for binding to the immobilized capture agents, and then washed thereafter allowing unbound sample to exit through an outlet channel;
    the immobilized transferrin is labeled with a labeling agent that is an antibody (fluorophore) which specifically binds transferrin;
    the capture/labeling chamber is washed with a buffer solution to remove spent/unreacted labeling agent (fluorophore);
    the capture/labeling chamber is again washed with a buffer of a non-denaturing detergent provided through the inlet to release bound transferrin from the mobilized capture agents into the IEF chamber;
    an isoelectrofocusing (IEF) chamber fluidically connected to the capture/labeling chamber, and comprising an IEF gel which separates proteins based on their pI; and
    a detector operatively connected to the isoelectrofocusing chamber configured to detect the presence of transferrin bands within the IEF gel, wherein the detection of beta-2-transferrin indicates the presence of CSF in the sample.

2. The microfluidic device of claim 1 wherein the detection of two transferrin bands indicates the presence of CSF in the sample.

3. The microfluidic device of claim 1 wherein the filter comprises a membrane, a mesh, a sieve, a gel or a column packing material.

4. The microfluidic device of claim 1, wherein the capture agent comprises an antibody, an aptamer, an affibody, an avimer, a peptide, or a transferrin receptor or fragment thereof.

5. The microfluidic device of claim 4, wherein the capture agent is an antibody that specifically binds transferrin.

6. The microfluidic device of claim 1, further comprising a reservoir containing a labeling agent, fluidically connected to the capture/labeling chamber.

7. The microfluidic device of claim 1, further comprising a reservoir containing a release reagent, fluidically connected to the capture/labeling chamber.

8. The microfluidic device of claim 7 wherein the release reagent comprises a non-denaturing detergent in an aqueous buffered solution, in an amount sufficient to release captured proteins from the immobilized capture agent.

9. The microfluidic device of claim 8 wherein the release reagent comprises a non-denaturing detergent in an aqueous buffered solution, where the buffer is compatible with iso-electrofocusing.

10. The microfluidic device of claim 1 wherein the detector is an LED or a photodetector grid array.

11. The microfluidic device of claim 10 wherein the LED or photodetector grid array is positioned on a single face of the IEF gel path.

12. The microfluidic device of claim 10 wherein the LED or photodetector grid array is positioned above and below the IEF gel path.

* * * * *